United States Patent [19]

Pohl et al.

[11] Patent Number: 4,855,273

[45] Date of Patent: Aug. 8, 1989

[54] ACID-RESISTANT CATALYSTS FOR THE DIRECT HYDROGENATION OF FATTY ACIDS TO FATTY ALCOHOLS

[75] Inventors: Joachim Pohl, Duesseldorf; Franz-Josef Carduck, Haan; Gerd Goebel, Erkrath, all of Fed. Rep. of Germany

[73] Assignee: Henkel Kommanditgesellschaft auf Aktien, Duesseldorf, Fed. Rep. of Germany

[21] Appl. No.: 162,537

[22] Filed: Mar. 1, 1988

[30] Foreign Application Priority Data

Mar. 2, 1987 [DE] Fed. Rep. of Germany ....... 3706658

[51] Int. Cl.$^4$ ............................................... B01J 23/72
[52] U.S. Cl. .................................... 502/244; 502/256; 502/524
[58] Field of Search ................. 502/244, 524, 256

[56] References Cited

U.S. PATENT DOCUMENTS

| | | | |
|---|---|---|---|
| 2,089,433 | 9/1934 | Salzberg | 23/236 |
| 3,173,959 | 3/1965 | Rittmeister | 260/638 |
| 3,193,586 | 7/1965 | Rittmeister et al. | 260/638 |
| 3,216,954 | 11/1965 | Howk et al. | 502/524 |
| 3,652,674 | 3/1972 | Hausen et al. | 502/244 |
| 3,756,964 | 9/1973 | Frazee et al. | 502/244 |
| 3,767,595 | 10/1973 | Montgomery | 502/244 |
| 3,899,577 | 8/1975 | Sugier | 423/656 |
| 4,134,905 | 1/1979 | Hasman | 260/409 |
| 4,158,665 | 6/1979 | Hasman | 260/409 |
| 4,199,479 | 4/1980 | Wilkes | 252/457 |
| 4,310,703 | 1/1982 | Tamaru et al. | 568/361 |
| 4,637,995 | 1/1987 | De Angelis et al. | 502/524 |

FOREIGN PATENT DOCUMENTS

| | | |
|---|---|---|
| 0023699 | 2/1981 | European Pat. Off. |
| 1005497 | 4/1957 | Fed. Rep. of Germany . |
| 2513377 | 1/1977 | Fed. Rep. of Germany . |
| 2613226 | 9/1977 | Fed. Rep. of Germany . |
| 3425758 | 4/1983 | Fed. Rep. of Germany . |
| 889791 | 10/1943 | France . |
| 1276722 | 10/1961 | France . |
| 124510 | 11/1971 | India . |

OTHER PUBLICATIONS

Chemical Abstract 57:16435i, p. 16435, vol. 57, Catalyst for Ester Reduction, Eastman Kodak Company; Chemical Abstract 88:22129t, Continuous Manufacture of Fatty Alcohols, Henkel and GmbH.

*Primary Examiner*—Carl F. Dees
*Attorney, Agent, or Firm*—Ernest G. Szoke; Wayne C. Jaeschke

[57] ABSTRACT

Process for the production of a new copper (II) chromite spinel catalyst using colloidal silica gel and to its use for the direct fixed-bed hydrogenation of fatty acids to fatty alcohols of corresponding chain length.

13 Claims, No Drawings

ACID-RESISTANT CATALYSTS FOR THE DIRECT HYDROGENATION OF FATTY ACIDS TO FATTY ALCOHOLS

BACKGROUND OF THE INVENTION

1. Field of the Invention

This invention relates to a new acid-resistant copper chromite spinel catalyst for the direct hydrogenation of fatty acids to fatty alcohols.

2. Statement of Related Art

Fatty alcohols, i.e. predominantly linear, monofunctional alcohols having chain lengths of 8 or more carbon atoms, and their production are described in detail in the literature, for example, in Ullmanns Encyklöpadie der technischen Chemie, 4th Edition, Vol. II, pages 427 to 445. Preferred starting materials for their production are the fatty acids and fatty acid mixtures occurring in natural fats and/or oils which may be converted to fatty alcohols of corresponding chain length by catalytic hydrogenation. Through the use of the fatty acids to be reduced in the form of their methyl esters, the catalysts in particular are protected against aggressive attack by the free carboxyl group, so that industrial processes can be operated for sufficiently long periods with satisfactory volume-time yields. Today, therefore, the predominant quantity of native fatty alcohols is produced from fatty acid methyl esters by a process in which the distilled methyl esters are passed in the liquid state, together with a large excess of hydrogen, over fixedly arranged copper-containing mixed oxide catalysts, such as for example copper/zinc catalysts, at temperatures above 200° C. and under pressures of from about 250 to 300 bar.

The copper-mixed oxide catalysts obtained by coprecipitation via the wet route are used as particulate catalysts or extrudates and, before use, are generally reduced in the plant or installation. They are not acid-resistant. Accordingly, it has not hitherto been possible in practice to produce native fatty alcohols by direct hydrogenation of the free fatty acids.

It is known from Ullman, loc. cit., that the hydrogenation of free fatty acids to fatty alcohols can be carried out by the suspension process using copper (II) chromite catalysts. However, this method can only be effectively used when the copper (II) chromite catalyst is obtained by decomposition of the copper ammonium chromate complex initially obtained and subsequent washing with acetic acid. Catalysts prepared in this way are particularly expensive and, in practice, can only be used for suspension hydrogenation. Acid-washed copper (II) chromite can only be tabletted with considerable difficulty, if at all, and accordingly cannot be converted into abrasion-resistant or mechanically strong extrudates or other shapes. Any attempt to achieve this increase in strength by after-annealing weakens the effect of the catalyst. Attempts to apply acid-washed copper (II) chromite to catalyst supports, such as silica gel or aluminium oxide for example also produces technically unuseable catalysts. The support is attacked and the catalyst is readily washed away.

According to the relevant patent literature, fatty acid esters, more especially fatty acid methyl ester, and free fatty acids are therefore simultaneously used as starting materials for the hydrogenation reaction to saturated and/or unsaturated fatty alcohols (cf. for example U.S. Pat. No. 3,193,586; U.S. Pat. No. 3,173,959; German Pat. Nos. 2,513,377 and 2,613,226). So far as industrial application is concerned the above processes have to be evaluated entirely differently according to whether the fatty acid esters of the free fatty acids are used as starting material for hydrogenation. It is generally known that the significant advantages of fixed-bed catalysis using solid catalysts do not apply to the processing of a starting material consisting of or containing free fatty acids. The corrosive effect of the free fatty acids at high temperatures and pressures on the solid catalysts which, basically, have been successfully used in the reduction of methyl esters is so great that it has not hitherto been possible to consider any of the above proposals for practical application in the reduction of free acids.

In practice, therefore, the situation is remedied by initially introducing relatively large quantities of fatty alcohol into the hydrogenation reactor and subsequently adding free fatty acid under hydrogenation conditions. However, this process requires relatively large reactors. It only achieves conversions of 96% whereas processes using fixed-bed catalysts achieve conversions of 99% and higher.

As discussed above, copper chromite catalysts are highly active catalysts for the hydrogenation of fatty acid esters and triglycerides of oils and fats. The direct hydrogenation of fatty acids with catalysts of this type has not hitherto been possible because copper (II) chromite ($CuCr_2O_4$) is not acid-resistant, i.e. is dissolved by the action of the free fatty acid. This applies in particular to the CuO present in the catalyst.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, an object of the present invention is to convert copper (II) chromite at high temperatures into an acid-resistant spinel form while maintaining as large a specific catalyst surface as possible and the corresponding pore structure which guarantees high activity and a high volume-time yield.

Accordingly, the present invention relates to a process for the production of an acid-resistant copper chromite spinel catalyst for the fixed-bed hydrogenation of fatty acids to fatty alcohols of corresponding chain length, wherein (a) silica containing copper (II) chromite ($CuCr_2O_4$) is prepared by dissolving a water soluble copper salt, e.g. the nitrate, preferably the nitrate salt, in water, optionally in the presence of other water soluble metal salts such as barium and manganese, also preferably in the form of their nitrate salts, adding thereto an aqueous colloidal solution of $SiO_2$ in a quantity such that from 0.1 to 15%, preferably 0.5 to 15%, and more preferably 4.5%, by weight of $SiO_2$ is present, based on the weight of the catalyst as a whole. The above salt-$SiO_2$ solution is then mixed with an aqueous chromic acid/ammonia solution in amount sufficient to convert all of the copper present to copper chromate, which precipitates out of the solution and contains the $SiO_2$ intimately admixed therewith;

(b) the copper chromate is washed free of soluble anions (e.g. nitrates) with water, dried, and calcined for at least 12 hours (e.g. from 12 to 24 hours) at a temperature of at least 750° C. (e.g. from 750° to 1000° C.).

In one embodiment of the present invention, the resulting calcined powder is mixed with from 0.5 to 10% by weight of an organic binder, such as for example polyvinyl acetate or methyl methacrylate, and from 0.5 to 15% by weight graphite, and the resulting mixture is granulated and subsequently tabletted; the percentages by weight being based on the weight of the mixture.

The present invention also relates to the acid-resistant copper (II) chromite spinel catalyst which has a silica gel content of from 0.1 to 15% by weight, based on the weight of the catalyst as a whole.

In one particular embodiment of the copper chromite spinel catalyst according to the invention, the silica gel content is 4.5% by weight.

The catalyst of the invention is suitable for the direct fixed-bed hydrogenation of fatty acids to fatty alcohols of corresponding chain length.

In one embodiment of the invention, $C_6$–$C_{24}$ fatty acid mixtures which can be obtained from animal and/or vegetable fats and/or oils are used as starting materials. The direct hydrogenation process according to the invention can be carried out using a ratio by volume of the quantity of catalyst to fatty acid mixture of from 0.1 to 3 per hour.

According to the invention, therefore, it is possible to use the known acid stability of copper (I) spinel for the direct hydrogenation of fatty acids to fatty alcohols on an industrial scale without, at the same time, having to accept losses in the volumetime yield. The pore volume time yields indicated in the literature for copper (I) spinels have been unexpectedly improved by the process according to the invention in which the porosity of the spinel is maintained.

In tests conducted with the new catalysts, it was found that an optimum in regard to activity and acid resistance is obtained when the $SiO_2$ content is 4.5% by weight.

In contrast to the copper (II) chromite catalyst, the copper (II) spinel catalyst according to the invention can readily be tabletted and, according, can be used as a fixed-bed catalyst.

Surprisingly, the process of the invention for the direct catalytic hydrogenation of fatty acids can also be improved by increasing the effectiveness of the catalyst by comparison with commercial catalysts through optimization not only of the chemical composition of the catalyst, as described above, but also of the physical structure of the shaped elements of the catalyst. By this is meant that, surprisingly, the physical structure of the shaped catalyst elements also has a considerable bearing on the activity and selectivity of the catalyst. According to the invention, an improvement in the process was obtained by tabletting the catalyst using 1 to 10% by weight of one or more binders. Compounds known from the prior art may be used for this purpose. One or even several binders may be present in the catalyst of the invention. It has proven to be particularly effective to use one or more binders from the group comprising polyvinyl acetate and methyl methacrylate. Polyvinyl acetate is preferably used as binder for the production of catalyst tablets; for example, commercially available 10% by weight polyvinyl acetate suspensions may be used for the production of the catalyst. The polyvinyl acetate suspensions are added in small quantities to the calcined, powder-form catalyst materials and mixed therewith until agglomerate grains begin to build up. Thereafter, the agglomerate-containing powder is compacted into small granulates, for example in a perforated roll granulator. The granulates are dried in known manner to residual moisture contents of from 10 to 15%. The resulting granulates are sieved and tabletted.

Before they are used in the direct hydrogenation of fatty acids, the catalyst used in the process of the invention are activated with hydrogen or with a hydrogen-containing gas mixture. A gas mixture predominantly consisting of a nitrogen/hydrogen gas mixture is advantageously used to activate the catalyst masses. As known from the prior art, such activation may advantageously be carried out by drying the catalyst masses in a stream of nitrogen at elevated temperature after their production and adding hydrogen in increasing quantities to the drying gas for activation. The hydrogen content of the activating gas mixture may be from 0.1 to 10% by volume. The catalysts may be activated both in situ and in vessels separate from the reaction vessel.

It is known that, depending on their origin, native fats and oils contained from relatively small to relatively large amounts of mono- or polyolefinically unsaturated fatty acids. Since the copper also saturates double bonds, saturated alcohols are also formed from unsaturated fatty acid esters.

By monitoring the quality of the end product of the process, the correct temperature can readily be selected in coordination with the ratio of recycled hydrogen to starting material. Excessively low process temperatures lead to a corrosive attack on the fixed-bed catalyst and hence to the discharge of metal soap via the reaction product. Both chromium soaps and also copper soaps may accumulate. Excessively high process temperatures lead to over-reduction and hence to an undesirably high formation of paraffins. Process temperatures are usually in the range of from 200° C. to 400° C., preferably in the range of from 250° C. to 300° C.

The reaction parameters to be adjusted in each individual case are co-determined inter alia by the length of the carbon chains of the fatty acids or fatty acid mixtures to be reduced. The shorter the chain length of the fatty acids used, the lower generally are the reaction temperatures within the ranges indicated.

In principle, lower alcohols, low-boiling paraffins or steam may be added to fatty acid starting materials used in accordance with the invention to modify the process conditions. However, provision must be made to ensure that the gaseous secondary reaction products formed are also removed from the reaction circuit and, in particular, from the recycled gas. The secondary reaction products are, in particular, the water formed during the reaction, small quantities of hydrocarbons and the quantities of nitrogen inevitably brought in with the hydrogen subsequently introduced.

The process is generally carried out under a pressure of 200 bar or higher and more especially under a pressure in the range of from 200 to 500 bar. In principle, the use of relatively high pressures leads to a reduction in the acid value of the reaction products and hence to an increase in the yield of the desired fatty alcohols.

The following examples illustrate but are not meant to limit the invention.

Example 1 below describes the production of a particularly suitable copper (I) spinel which is used in Examples 2 and 3.

EXAMPLE 1

85 g barium nitrate, 294 g manganese nitrate and 2493 g copper nitrate were dissolved in 9 liters deionized water. 550 g of a 40% SiO$_2$ colloid were added to the clear solution. The mixture was heated to 70° C.

In a second stirring vessel, 1639 g chromic acid were dissolved in 9 liters water. 3600 g of a 25% ammonium solution were added to the resulting solution. The solution was heated to 70° C. The copper chromate was precipitated by addition of the Cu, Ba, Mn nitrate solution to the ammonium chromate solution introduced beforehand. The filter cake was washed free from nitrate and dried. Calcination was carried out for 12 hours at 750° C. The powder was then mixed with 2% polyvinyl acetate and 2% graphite, granulated and tabletted (4×4 mm tablets).

EXAMPLE 2

12 g powder of the catalyst prepared in accordance with Example 1 and 600 g C$_{12}$ fatty acid were reacted in a 2 liter autoclave at a temperature of 260° C. under a hydrogen pressure of 250 bar. The following fatty acid conversions were determined after 1, 3 and 5 hours.

| Reaction time (h): | 1 | 3 | 5 |
|---|---|---|---|
| FA conversion (%): | 39 | 48 | 75 |

The catalyst was not dissolved during the hydrogenation reaction.

EXAMPLE 3

In a tube reactor, tablets (4×4 mm) in volume of 500 ml were reduced with an H$_2$/N$_2$ mixture (H$_2$: N$_2$=1:10) at 200° C. The catalyst was carefully warmed up with C$_{12}$–C$_{18}$ fatty acid methyl ester. 400 to 500 1 C$_{12}$ fatty acid per hour were then pumped over the catalyst under a hydrogen pressure of 250 bar and at a temperature of 260° to 275° C. The effluents were water-clear. The following values were determined:

| Acid value: | 0.04 |
|---|---|
| Saponification value: | approx. 2 |
| Hydroxyl value: | 285 to 293 |

We claim:

1. A process for the production of an acid-resistant copper chromite spinel catalyst consisting essentially of copper (II) chromite and silica wherein copper (II) is the only metal ion present therein comprising the steps of:
   (a) dissolving a water soluble copper salt in water to form an aqueous solution thereof,
   (b) mixing the above aqueous solution with an aqueous colloidal solution of SiO$_2$,
   (c) mixing the solution resulting from step (b) with an aqueous chromic acid/ammonia solution in amount sufficient to form a precipitate of substantially all of the copper present as copper chromate,
   (d) washing the precipitated chromate with water to remove soluble anions therefrom,
   (e) drying the copper chromate, and
   (f) calcining the copper chromate for at least about 12 hours at a temperature of at least about 750° C. to produce silica containing copper (II) chromite;
   wherein in step (b) the SiO$_2$ is present in a quantity of from about 0.1 to about 15% by weight, based on the weight of the catalyst as a whole.

2. The process of claim 1 wherein in step (a) the water soluble copper salt is the nitrate salt.

3. The process of claim 1 wherein from about 0.5 to about 15% by weight of SiO$_2$ is present in step (b).

4. The process of claim 1 wherein about 4.5% SiO$_2$ is present in step (b).

5. The process of claim 1 wherein the silica containing copper (II) chromite from step (f) is then mixed with from about 0.5 to about 10% by weight of an organic binder, and from about 0.5 to about 15% by weight of graphite, based on the weight of the mixture, and the mixture is then granulated and formed into tablets.

6. The process of claim 5 wherein the organic binder is polyvinyl acetate or methyl methacrylate.

7. An acid-resistant copper (II) chromite spinel catalyst containing intimately admixed therewith from about 0.1 to about 15% by weight of SiO$_2$, based on the weight of the catalyst as a whole.

8. The catalyst of claim 7 wherein from about 0.5 to about 15% SiO$_2$ is present therein.

9. The catalyst of claim 7 wherein about 4.5% SiO$_2$ is present therein.

10. An acid-resistant copper (II) chromite spinel catalyst in tablet form comprising
    A. copper (II) chromite containing intimately mixed therewith from about 0.1 to about 15% by weight SiO$_2$, based on the total weight of catalyst,
    B. from about 0.5 to about 10% by weight, based on the total weight of catalyst, of an organic binder, and
    C. from about 0.5 to about 15% by weight, based on the total weight of catalyst, of graphite.

11. The catalyst of claim 10 wherein the organic binder is polyvinyl acetate or methyl methacrylate.

12. The catalyst of claim 10 wherein in component A. from about 0.5 to about 15% by weight of SiO$_2$ is present.

13. The catalyst of claim 10 wherein in component A. about 4.5% SiO$_2$ is present.

* * * * *